(12) United States Patent
Cosentino et al.

(10) Patent No.: US 12,736,450 B2
(45) Date of Patent: Sep. 15, 2026

(54) PORTABLE MOTORIZED PRESSUREMETER AND METHOD FOR CALCULATING IN SITU SOIL PROPERTIES

(71) Applicant: Cosentino Engineering Instrumentation Services, LLC, Palm Bay, FL (US)

(72) Inventors: Paul J. Cosentino, Palm Bay, FL (US); Thaddeus J. Misillo, III, Palm Bay, FL (US); Anuar Akchurin, Melbourne, FL (US); Brhane Weldeanenya Ygzaw, Bloomfield, NJ (US)

(73) Assignee: Cosentino Engineering Instrumentation Services, LLC, Palm Bay, FL (US)

( * ) Notice: Subject to any disclaimer, the term of this patent is extended or adjusted under 35 U.S.C. 154(b) by 0 days.

(21) Appl. No.: 19/644,812

(22) Filed: Apr. 10, 2026

(65) Prior Publication Data

US 2026/0243639 A1 Aug. 20, 2026

Related U.S. Application Data

(63) Continuation-in-part of application No. 18/613,944, filed on Mar. 22, 2024, now abandoned.

(Continued)

(51) Int. Cl.
*G01N 3/12* (2006.01)
*G01N 33/24* (2006.01)

(52) U.S. Cl.
CPC ............... *G01N 3/12* (2013.01); *G01N 33/24* (2013.01)

(58) Field of Classification Search
CPC .. G01N 3/08; G01N 2203/0075; G01N 33/24; G01N 2203/025; G01N 2203/0266;

(Continued)

(56) References Cited

U.S. PATENT DOCUMENTS 3,442,122 A 5/1969 Thorley
3,858,441 A 1/1975 Comeau (Continued)

OTHER PUBLICATIONS

Alaa Mohammed Shaban, Evaluation of Unbound Pavement Layers Moduli Using the Miniaturized Pressuremeter Test, May 2016 (Year: 2016).

(Continued)

*Primary Examiner* — Kristina M Deherrera
*Assistant Examiner* — Gedeon M Kidanu
(74) *Attorney, Agent, or Firm* — Steinberger IP Law; Brian S. Steinberger; Hilary F. Steinberger

(57) ABSTRACT

Portable motorized pressuremeter system, device and method calculating soil strengths and stiffnesses. The system uses a controller, external water supply and balloon probe. Controller houses a data acquisition card, electric motor with encoder, hydraulic pump, pressure transducer, rechargeable battery. A ground engaging balloon probe is placed into a soil borehole. A switch is activated and the computer drives the encoded electric motor to pump water via saturated tubing via the pump to radially inflate the balloon in up to approximately 20 equal volume increments until the balloon is approximately 50% larger than an initial filled position in the borehole. In a single operation that runs within approximately five minutes, the motor moves water through the pump to apply pressure on the borehole walls, while pressure and volume are recorded at each fluid injection increment. The computer accurately calculates soil stiffness and soil strength for the soil around the borehole.

20 Claims, 15 Drawing Sheets

Related U.S. Application Data

(60) Provisional application No. 63/454,119, filed on Mar. 23, 2023.

(58) Field of Classification Search
CPC .... G01N 3/10; G01N 3/12; G01N 2203/0048; G01N 2203/0082; G01N 2203/0244; G01N 3/02; G01N 3/064; E21B 49/006; E21B 47/06; E21B 43/105; E21B 43/108; E21B 49/00; E21B 7/20; E21B 49/008; E21B 17/00; E02D 1/022; E02D 1/027; E02D 2450/10; G06F 2119/06; G06F 30/13; G06F 30/20
See application file for complete search history.

(56) References Cited

U.S. PATENT DOCUMENTS

| | | | | |
|---|---|---|---|---|
| 4,043,186 | A | 8/1977 | Marchetti | |
| 4,326,409 | A | 4/1982 | Hughes | |
| 4,492,111 | A | 1/1985 | Kirkland | |
| 4,545,702 | A | 10/1985 | Sano | |
| 4,979,197 | A | 12/1990 | Troxler, Sr. | |
| 5,540,101 | A | 7/1996 | Capelle | |
| 6,560,550 | B2 | 5/2003 | Omar | |
| 8,776,583 | B2 * | 7/2014 | Marchetti | E02D 1/022 73/84 |
| 10,823,880 | B1 | 11/2020 | Gupta | |
| 11,566,985 | B1 * | 1/2023 | Gupta | E02D 1/022 |
| 11,862,843 | B1 * | 1/2024 | Immer | H01Q 1/1228 |
| 2004/0095154 | A1 | 5/2004 | Lundstrom | |
| 2009/0245018 | A1 | 10/2009 | Marchetti | |
| 2011/0194672 | A1 | 8/2011 | Troxler | |
| 2024/0003863 | A1 | 1/2024 | Duncan | |

OTHER PUBLICATIONS

Paul J. Cosentino and Thaddeus J. Misilo III, Comparing Engineering Properties of Small Diameter Pressuremeter Tests to Clegg Impact Hammer Tests in Cemented Coquina Base and Sandy Subgrades, ASTM Geotechnical Testing Journal, Paper GTJ 2019-0421, Sep. 1, 2021, vol. 55, Issue 5; totaling 19 pages.

Roctest Instruction Manual Pressuremeter Model PENCEL, Roctest Limited 2016 (Year: 2016); totaling 12 pages.

Roctest Texam Pressuremeter Instruction Manual, retrieved from https://roctest.com/wp-content/uploads/2018/02/E1001E-20240426.pdf on Feb. 18, 2026; totaling 34 pages.

Roctest Texam Pressuremeter Instruction Manual, Roctest Limited, 2017 (Year: 2017); totaling 28 pages.

Troxler Model 3430 and 3440 Moisture Density Gauges, retrieved from https://troxlerlabs.com/wp-content/uploads/2022/10/3430-3440plus-20Aug2019.pdf on Apr. 9, 2026; totaling 4 pages.

Florida Tech Automated Pressuremeter, National Instruments LabVIEW 2015, Version 15.0.1f1 (32-bit). (Year: 2018); totaling 1 page.

* cited by examiner 140
120
100
80
60
40
20
0
Limit Pressure, pL (psi)
80
90
100
110
120
130
140
Dry density (pcf)

SSMiniPMT Side View (Control Unit Including Supports)

SSMiniPMT Component Supports
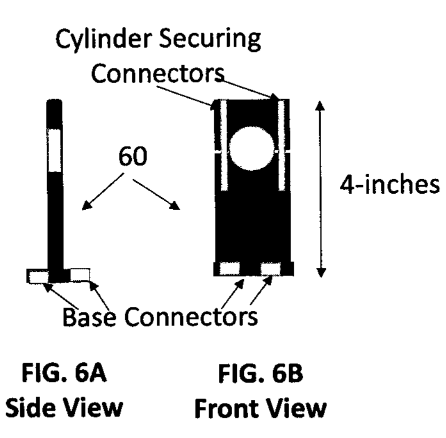
FIG. 6A
Side View
FIG. 6B
Front View
Cylinder-Piston Support System
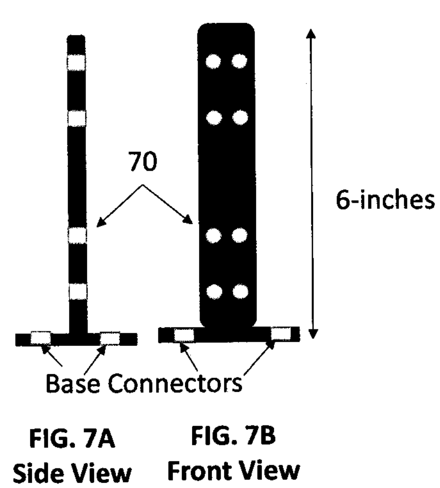
FIG. 7A
Side View
FIG. 7B
Front View
Electric Motor Supports SSMiniPMT Top View (excluding supports)

FIG. 10B
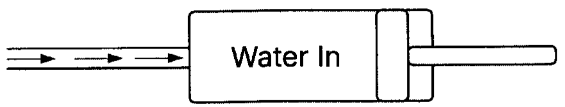
Fully Retracted Hydraulic Cylinder (Water Injector)
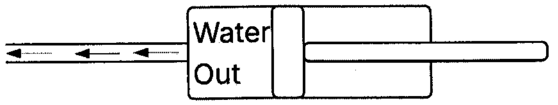
Partially Extended Hydraulic Cylinder (Water Injector)
FIG. 10C

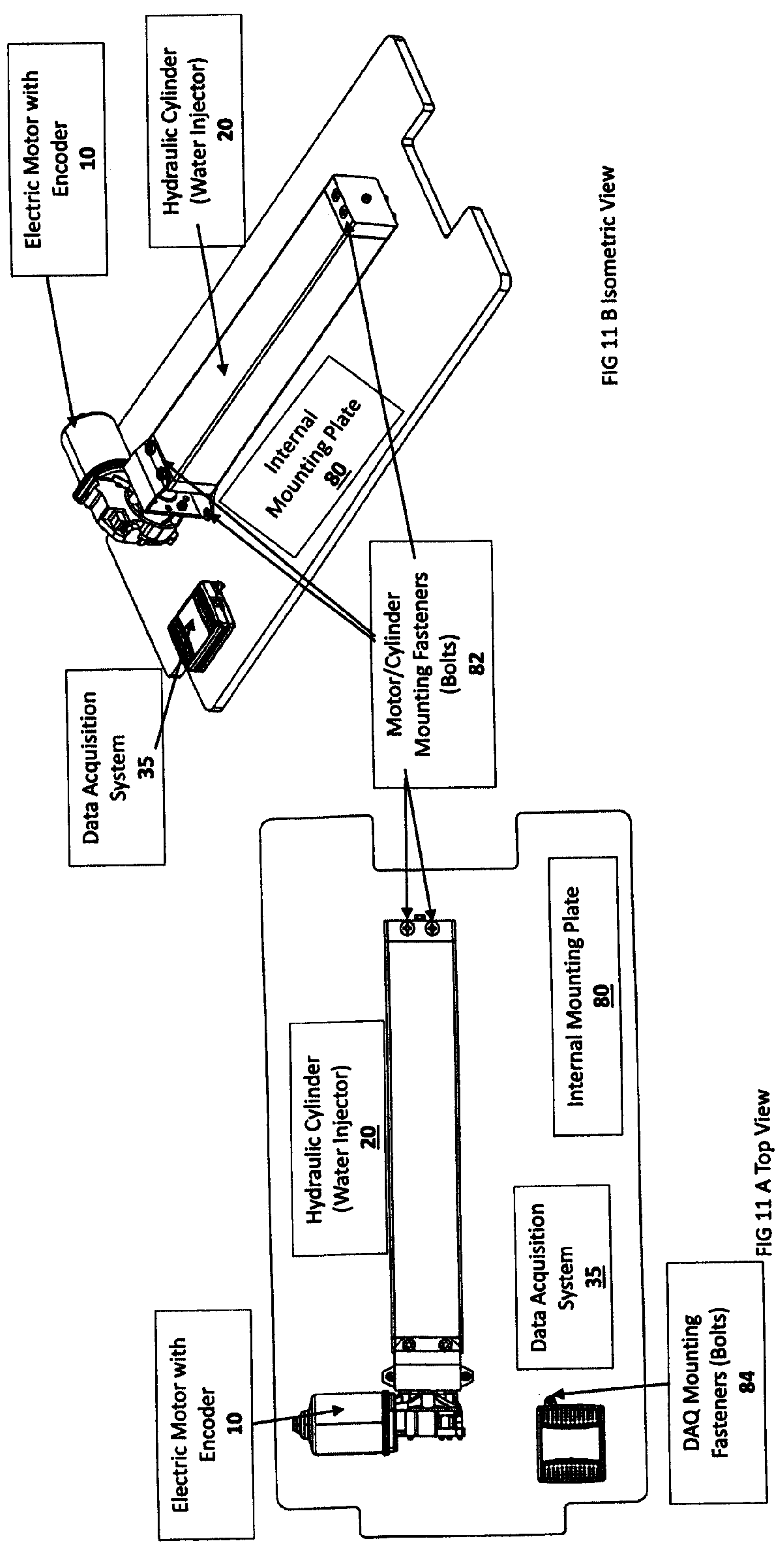
FIG 11 B Isometric View
FIG 11 A Top View

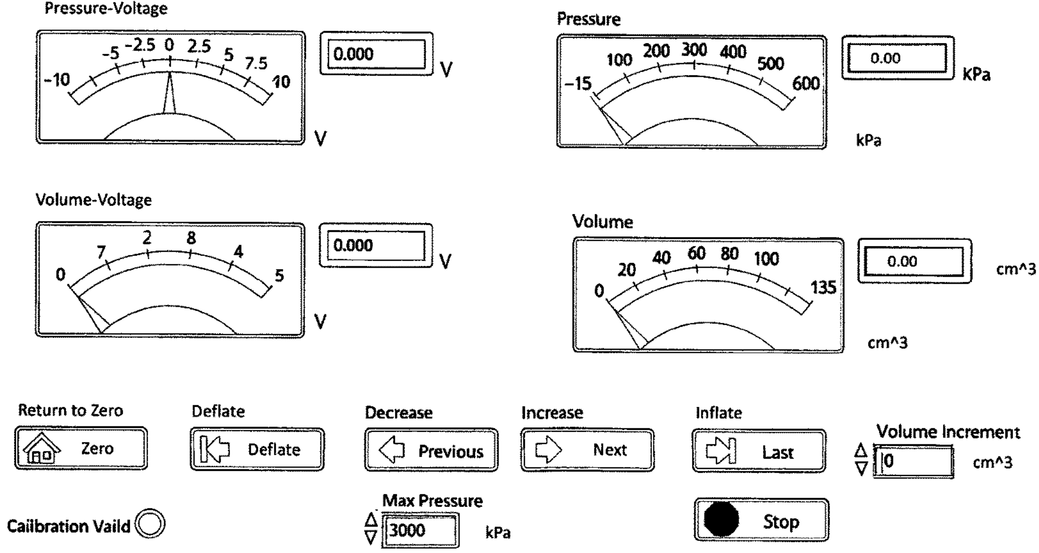
FIG. 12 Motorized APMT© internal sensor equipment indicator checks with key pressure and volume inputs

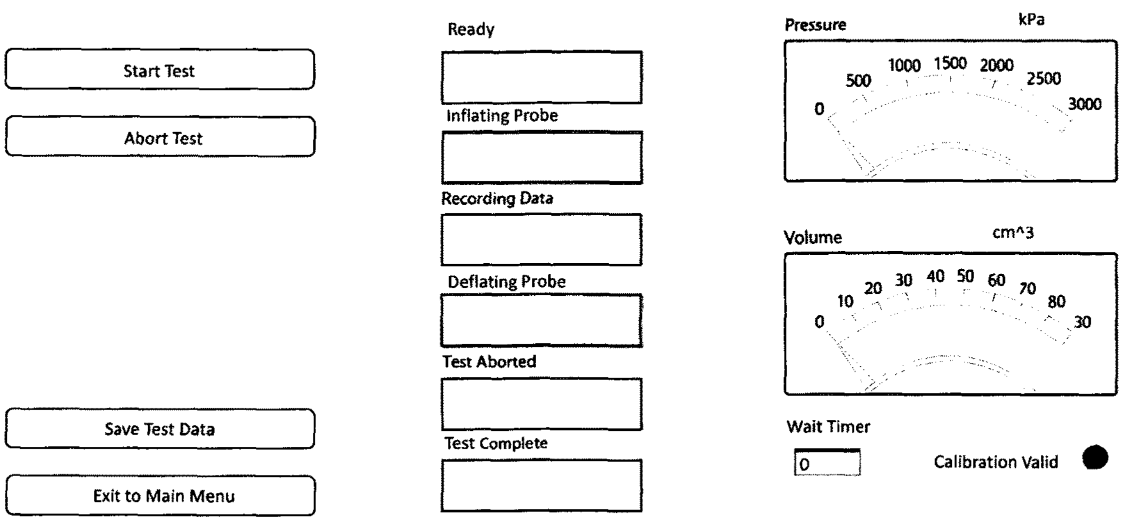
FIG. 13 APMT© screen showing screen pressure, volume and testing indicators during motorized tests

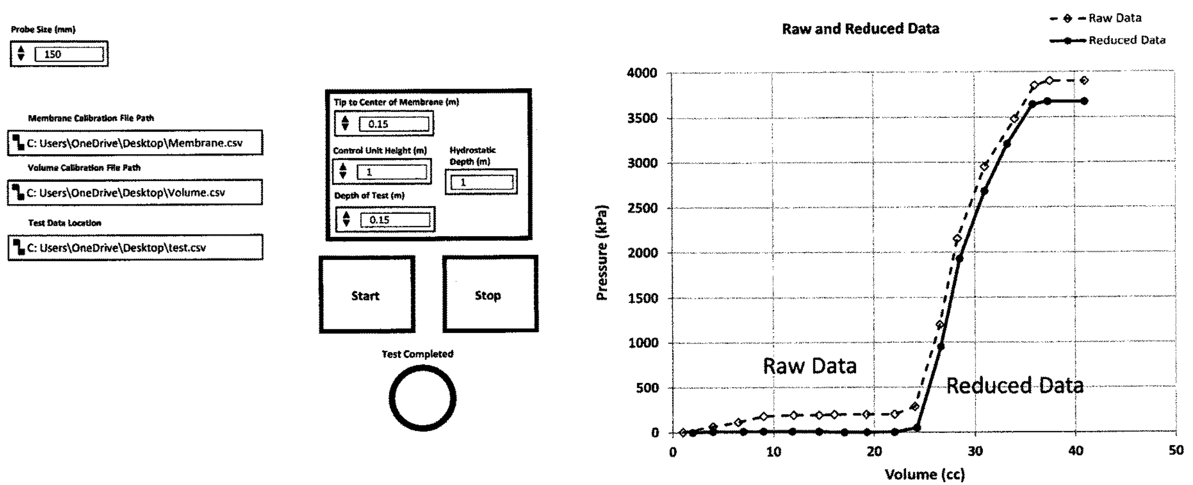
FIG. 14 Motorized APMT© testing screen with raw test data and corrected or reduced test data following membrane and volume calibration adjustments

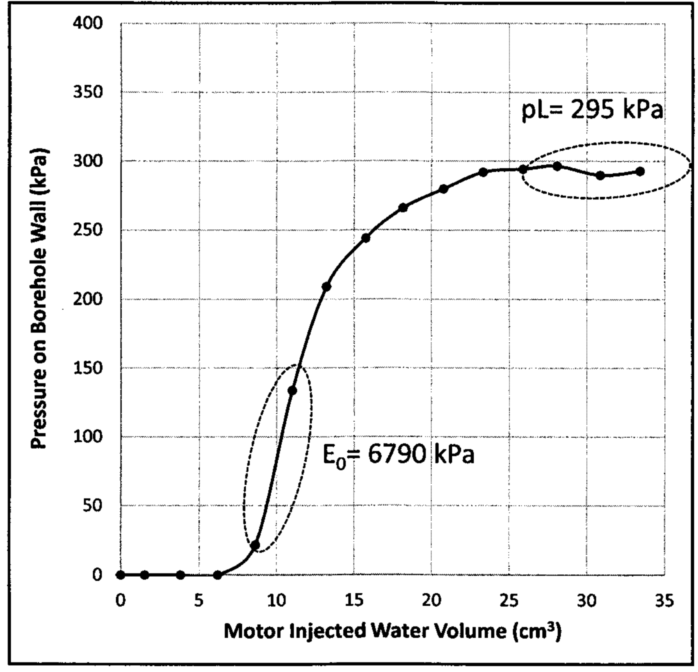
FIG. 15 Motor Operated PMT Test on Soil

PORTABLE MOTORIZED PRESSUREMETER AND METHOD FOR CALCULATING IN SITU SOIL PROPERTIES

CROSS REFERENCE TO RELATED APPLICATIONS

This application is a Continuation-In-Part of U.S. patent application Ser. No. 18/613,944 filed Mar. 22, 2024, which claims the benefit of priority to U.S. Provisional Application Ser. No. 63/454,119 filed Mar. 23, 2023, the entire disclosure of which is incorporated herein by specific reference thereto.

FIELD OF INVENTION

This invention relates to measuring soil strengths and/or stiffnesses/and/or deformations, and in particular to devices, apparatus, systems, and methods for providing a portable compact fully automated pressuremeter (PMT) and method to perform a soil balloon test with a probe placed into the soil, and automatically and instantly calculate accurate soil strengths and soil stiffnesses values at different in-situ soil locations in a single operation.

BACKGROUND AND PRIOR ART

Field compaction quality control (QC) of soils is the most common testing performed by the geotechnical community. Compaction specifications require a specified density and moisture content to be achieved; however, moisture and density are what we term as index properties only producing a general idea that a material will perform adequately. Engineers would be more confident in their designs and construction if they used the in-situ stress-strain behavior to determine the soils' stiffness and strength (i.e., modulus and limit pressure).

Nuclear density gauge (NDG) testing, where a ⅝th inch diameter radioactive probe is inserted into a ¾ inch diameter 2-, 4-, 6-, 8-, 10- or 12-inch-deep preformed hole, and the emitted radiation is recorded in an instrumented lead-encased 35-pound unit, to produce the in-situ soil moisture and density. With accessories, NDG equipment is carried in a 50-pound transport box around construction sites. Its testing requires skilled and licensed operators, plus significant logistical tracking, and nuclear regulatory paperwork. Replacing NDG testing with equipment that produces strength, and stiffness would be a major cost-effective and engineering improvement.

When placing concrete or hot-mix asphalt, samples obtained for quality control (QC) testing ensure these materials meet specified minimum strength requirements. Concrete and asphalt have fixed densities but have a very large range of strengths. Because of soils' nonlinear stress-strain behavior during loading both the strength and stiffness are critical. As with both asphalt and concrete, various strengths and stiffnesses can be associated with a fixed soil density. However, we fail to measure either stiffness or strength during placement.

The in-situ soil testing device, known as a pressuremeter (PMT), has been available to the geotechnical engineering community for decades. It can be described as a long cylindrical balloon that when properly placed in the soil and expanded with water, or similar fluid, produces the most informative soil behavior data possible. However, performing tests always requires a highly skilled operator. PMT data, from high quality tests, displayed as pressure on the soil versus probe a) volume, b) volumetric strain or c) radial strain, can be used for a wide range of geotechnical and pavement engineering problems. These problems include, but are not limited to, predicting settlement of footings, lateral capacity of driven piles and drilled shafts, pavement layer strengths and stiffnesses, general fill compaction strengths and stiffness, etc. The basic limitations from this test are the required operator skills and the placement of the PMT probe in the soil. If the testing process can be simplified, the soil placement would be its only remaining drawback.

PMT testing is one of a group of in-situ soil tests, which include cone penetrometer, dilatometer, vane shear, and the standard penetration test. All in-situ tests face the same instrument placement concerns. The equipment used to control the cone and dilatometer tests has been upgraded such that, after proper placement in the soil, the operator simply pushes a button on a computer screen to record the data. The standard penetration test is not automated and produces inconsistent data as a result. Vane shear testing is not commonly used and therefore, the demand for improving its testing process is not high enough to motivate companies to invest in it.

PMT test data is represented using the soil stress versus strain response as its long cylindrical balloon is gradually expanded into the surrounding soil. From this stress-strain information the soil behavior, in terms of stiffness or soil modulus (E) and strength in terms of the soil ultimate strength or limit pressure (pl), is found and used for new designs and existing evaluations. However, it is possible to determine many other critical engineering behavior information from this same test. This additional data is not typically determined simply because it requires a highly skilled test operator.

FIG. 1A is a graph with PMT and NDG data from the prior art devices shown in FIG. 2 and FIG. 3 it displays the initial modulus, Eo (psi) versus soil dry density (pcf). FIG. 1B is a graph of PMT and NDG data from the prior art devices of FIG. 2 and FIG. 3, it displays the PMT limit pressure pl (psi) versus soil dry density (pcf). The PMT modulus and limit pressure data are determined using basic elastic theory which is applied to describe material load-deformation behavior.

The data in FIG. 1A and FIG. 1B show that both the PMT modulus (stiffness) and strength (limit pressure) vary significantly at a given density. For example, at a density of 100 pounds per cubic foot (pcf), stiffness varies from below 200 to over 1400 pounds per square inch (psi), while the strength varies from less than 10 to nearly 80 psi. The 7-to-8-fold range of values at one density show that density does not help engineers understand the variation in stiffness and strength of in situ soils and therefore is not the best tool for evaluating soil engineering behavior.

QC acceptance criteria for soil compaction has remained the same for over 60 years, as field compaction data, reported in terms of moisture and density are checked against standards lab based tests. Although lab-based soil compaction testing is relatively simple and consistent; no stress-strain, stiffness or ultimate strength data are derived from it.

The most common field compaction QC test is NDG testing, which is an expensive, government-regulated test with regulations that produce serious logistical problems for all geotechnical and pavement consultants.

NDG equipment initially costs approximately $9,000 to $10,000 while annual licensing costs an additional $2,000 to $2,500. Annual calibrations run an additional $500. Proper storage and paperwork can cost thousands more each year.

Finally, disposal of the nuclear source can range from $2,000 to $5,000 depending upon the make and model. Logistically, NDG storage requires several layers of security, and the ability to recharge the equipment. A civil engineering consulting firm reported spending $1,100,000 on NDG paperwork for their 70 gauges in one year, or over $15,000 per gauge.

The typical prior art 50-pound nuclear density gauge (NDG), shown in FIG. 2, has a ⅝th inch diameter radioactive probe that is inserted into a preformed hole made by driving a ¾-inch steel pin between 2- and 12-inches into the soil. The equipment requires charging each night in a locked facility and daily calibrations on a heavy standard calibration block.

NDG testing has been the accepted quality control soil compaction test for nearly 6 decades. It is fast and produces reliable moisture and density results. Engineers specify minimum field density levels based on very commonly performed laboratory compaction tests known as Proctor compaction tests.

However, two significant problems have been ignored. First, density is not strength and stiffness, which is what engineers desire to know. Our geotechnical engineering industry has accepted the concept that higher density implies stronger materials, but strength is not measured by this device. Density does not help engineers clearly understand the engineering behavior of compacted materials, as any material with one density can have a large range of strengths, like concrete with a density of 150 pounds per cubic foot can have strengths from 2,000 to 20,000 pounds per square inch.

Density is merely a qualifier that is easy to measure with these radioactive devices. Secondly, as the name implies, a radioactive probe is used, which leads to a significant amount of regulatory paperwork which translates into significant logistical costs.

These gauges have been stolen or involved in various types of accidents. When these occur, the Nuclear Regulatory Commission (NRC) becomes heavily involved, resulting in construction delays and significant cost increases.

Various types of soil testing probes have been proposed over the years, in patents and published patent applications but have failed to become practical solutions to determine soil strengths and/or stiffnesses/and/or deformations of the soil. See U.S. Pat. No. 4,326,409 to Hughes and 4,979,197 to Troxler, Sr. et al., which are incorporated by reference in their entirety. See U.S. Published Patent Applications: 2004/0095154 to Lundstrom et al.; and 2011/0194672 to Troxler, which are incorporated by reference in their entirety.

In 2016, a dissertation entitled "Evaluation of Unbound Pavement Layers Moduli Using the Miniaturized Pressuremeter Test" was presented by doctoral student Alaa Mohammed Shaban, at the Florida Institute of Technology in Melbourne, Florida. Dr. Paul Cosentino, a co-inventor of the subject invention, was his primary advisor and Doctoral Committee Chair for the Department of Civil Engineering at the Florida Institute of Technology at that time.

Shaban did not develop any equipment for commercial use. All his work required a very highly skilled operator to produce data. If the skill level of the operator was insufficient, then none of the results obtained by Shaban would have been achieved.

The Miniaturized PMT Controller Shaban used was purchased from Roctest Limited in Montreal, Canada and upgraded to yield digital pressure and volume data. Even after the upgrades, it required operation by hand using a hand crank or handle that was rotated. This rotation was required to inject a specified amount of water into the probe. A series of equal water injections was required for each test. The testing performed in Shaban was research-based testing to allow the data to be used for pavement design and evaluation purposes. Well over 40 data points were recorded per test with most being a result of injecting water in equal increments. Cyclic loading and unloading increments were included with data to be used to simulate vehicles passing over the pavement.

Additional unloading increments were also performed in Shaban to evaluate how modulus varies with the amount of strain. To record each data-point, the rotation had to be stopped by hand at the specified volume of water, a computer with specialized software called APMT© (which stands for Automated Pressuremeter Test) had to be used to record the data point and the handle was rotated to the subsequent water volume. This software was developed by Thaddeus J Misilo III the co-inventor of this patent during 2006 research sponsored by the Florida Department of Transportation Research. To record one point typically between 30 and 60 seconds elapsed after the water was injected. To properly run tests Dr. Shaban was trained for several months. An operator with a high school education would not have been able to produce any of the results given in the Shaban dissertation.

The hand crank system used by Shaban required the operator to turn the control unit volume injection handle and not only inject equal volumes of water into the balloon, but to do so at a constant rate. Shaban was required to inject 5 $cm^3$ of water during each loading sequence at a constant loading rate of approximately 5 seconds. The accuracy of this process was limited by the precision of the handle-socket system connected to the injection cylinder, the analogue volume counter mounted on the control unit and the gearing used between the handle counter and the cylinder.

Not only do these components affect the accuracy of the injection, but as the soil strength and stiffness changes from low to high, it becomes much more difficult to turn the handle and inject water at a constant rate. Tests in high-strength soil often require the operator to use both hands to turn the handle. It is extremely difficult to precisely inject water when using both hands, while turning the handle at high torques. This difficulty often results in excess water being injected during the corresponding testing increments.

The Shaban dissertation is not able to produce precise 5 $cm^3$ volumes of water since injection requires turning the handle while reading the analogue volume counter, which has an accuracy of 0.1 $cm^3$. Operators are only able to ensure an accuracy of +/−0.05 $cm^3$.

To properly complete PMT tests with the Shaban PMT, the probe volume (i.e., rubber cylindrical balloon) must be increased in size by about 50 percent. The probe is constructed with a fixed length; therefore, any volume increases only occurs due to increases in the probe diameter. During tests the increase in the pressure on the soil and volume of the balloon from about 20 data points are recorded. The process in the Shaban dissertation requires a highly skilled operator. Shaban was trained for several months to learn how to properly inflate and deflate the probe using the handle.

There is evidence of many strain-controlled PMT tests run by engineering consulting firms where as few as five or six data points were recorded during a single test, which are not enough, making them unusable for the engineer.

Even by employing highly skilled operators, the PMT data taken in the Shaban dissertation required injection produced by the hand crank technique and is poor quality.

It would be impossible for the Shaban PMT to be used by a field technician to provide in-situ soil deformation and strength calculations in less than many hours. It would be clearly impossible to use or modify the Shaban PMT to provide in situ soil strength and deformation calculations within approximately 30 seconds which is achieved by the subject invention. The cost of the field technician at $20 to $40 per hour to use the subject invention to determine in situ deformation and strength calculations would be a fraction of the over $200 per hour required by the skilled PhD required to use the Shaban PMT.

The Shaban PMT would require a skilled operator in the field such as one having a PhD plus at least approximately 90 minutes to produce accurate calculations of in-situ soil deformation and strength properties. Experts in the art, such as an operator with a PhD, who would need to charge at least $200 per hour, which would cost at least $300 for their time alone for determining in situ soil deformation and strength calculations for one site. These calculations are necessary for generally every location where commercial construction is necessary. For example, every new Amazon warehouses and distribution center would require several hundred such in-situ soil deformation and strength calculations for construction at each location. As such, it is not possible nor practical to use the Shaban PMT in the field, as it requires a highly skilled operator and therefore would be cost-prohibitive.

In 2018, a dissertation entitled "Development of a Small Diameter Rapid Pressuremeter Test for Unbound Pavement Layer Evaluations" was presented by doctoral student Thaddeus J Misilo III, at the Florida Institute of Technology in Melbourne, Florida. Dr. Paul Cosentino, a co-inventor of the subject invention, was his primary advisor and Committee Chair for the Department of Civil Engineering at the Florida Institute of Technology at that time. The main results from his work were compiled into two publications and Dr. Paul Cosentino is the main author for both publications (Cosentino and Misilo 2020, 2022).

The Small Diameter PMT Controller Misilo used was purchased from Roctest Ltd in Montreal, Canada and upgraded to yield digital pressure and volume data. This probe was later renamed to SSMini, standing for a miniature probe that produces both strength and stiffness. The main objective of this work was to investigate how a $5/8^{th}$ inch diameter probe 6- and 12-inches long would work for compaction quality control issues. Misilo proved that the data from both 6- and 12-inch $5/8^{th}$ diameter probes were useful for evaluating the compaction quality of soils. His data was compared to NDG dry unit weights, stiffnesses from two lightweight deflectometer models, Clegg impact hammer stiffness and dynamic cone tests.

The subject co-inventor on this patent application, Dr. Thaddeus Misilo III, experienced this problem firsthand during his dissertation work. As he used the same controller as Shaban and tested very strong pavement base materials with the SSMini 6- and 12-inch long ⅝ths inch diameter probes, Misilo III was forced to use two hands while turning the handle during the injection processes in these strong soils. The resulting injection rate variations produced engineering analysis problems from his results proving that even a highly skilled operator cannot maintain a constant injection rate as the soil strengths and stiffnesses change. Paul J. Cosentino and Thaddeus J. Misilo III. Comparing Engineering Properties of Small Diameter Pressuremeter Tests to Clegg Impact Hammer Tests in Cemented Coquina Base and Sandy Subgrades, ASTM Geotechnical Testing Journal, Paper GTJ 2019-0421 Sep. 1, 2021, Vol. 55, Issue 5.

Results from Misilo were used as the basis for the motorized controller as he is the co-inventor for this patent application. There was no motor used in any of his testing, completed by 2018. This small diameter equipment was a first attempt at replacing the nuclear density test. It proved that the concept was possible but that a motor was required to produce results. As stated above Misilo could not accurately control the injection rates during his testing, especially when hard or stiff soils were encountered.

Roctest DMP/DMPe borehole Dilatometer U.S. Pat. No. 5,540,101 to Capelle et al., which is incorporated by reference, describes a borehole dilatometer for in situ rock mass deformability testing. It is lowered into a 96 mm or 101 mm (approximately 4-inch diameter) borehole. Then an inflatable membrane is manually pressurized with compressed dry gas, typically nitrogen, in progressive pressure steps while the internal probe feelers measure the resulting diametrical deformation of the borehole wall. Its stated purpose is to determine parameters such as global deformation modulus, elastic modulus from cyclic loading, creep parameters, and rock anisotropy, and it is designed for applications such as tunnels, underground storage, mines, and large civil engineering structures. The probe includes an inflatable membrane with metallic inserts, three pairs of inductive displacement sensors, a pressure sensor, a reference sensor for temperature compensation, and a sediment collector. The electronic DMPe version adds automatic data acquisition and real-time visualization through a Datalogger (D/P Box) readout operated by an Android tablet, with Bluetooth communication and spreadsheet-compatible CSV output. The combination of direct wall-contact sensing through solid inserts in the membrane eliminates calibrations to produce the deformation modulus. This system is compatible with deep boreholes greater than 100 m. Its main limitation is that it is a manually controlled gas-pressurized, stress-controlled system operated from the surface using valves, pneumatic tubing, and electrical cable, rather than a motor-driven internal fluid-displacement system. Stress-controlled testing produces less data than its counterpart strain-controlled testing. Smaller movements (i.e., strains) can be applied during strain-controlled tests, producing many more data points to more precisely describe the stress-strain behavior of the soil.

U.S. Pat. No. 4,326,409 to Hughes, which is incorporated by reference, describes a Bore Hole Test Probe that is a manually operated in-situ borehole expansion testing device intended to measure the mechanical response of soil or rock surrounding a drilled borehole. The probe consists of a hollow cylindrical body covered by a flexible membrane that expands outward when manually pressurized so that the membrane contacts the borehole wall. The device is connected to a compressed gas source which is manually controlled during pressurization. The outward movement of the membrane is monitored using feeler members equipped with strain gauges, which measure the radial displacement of the borehole wall as the pressure increases. These stress-controlled displacement measurements allow estimation of the deformation characteristics of the surrounding ground material. The probe functions as a pressuremeter-type expansion device where deformation is measured as the membrane expands against the borehole wall. This system is a surface-stress controlled pressure device, meaning the pressurization mechanism and operational control occurs outside the probe and produces less accurate data than strain-controlled tests. This patent does not describe any motorized or automated pressurization system, and the operation depends on manually controlling the external pressure supply at the surface.

U.S. Pat. No. 6,560,550 to Omar, which is incorporated by reference, describes a probe and a computer designed to indirectly measure the indirect tensile strength or deformation characteristics of weak rock or hard soil. The approximately 3-inch-long probe with a measuring length of about 1.5 inch and about ½ inch outside and 1/16$^{th}$ inch inner diameter probe consists of a rigid probe body with an internal fluid passageway and an expandable flexible membrane that surrounds the probe. Once inserted into a previously drilled borehole, fluid pressure is applied to inflate the rubber membrane using a control unit with a pump. A computer with preloaded software is then used to determine the tensile strength indirectly. The probe expands outward against the borehole wall until failure to complete a test. During testing, the operator manually applies controlled pressure increments and records the corresponding volume changes of the membrane, until sudden tensile failure. These pressure-volume data are used with the computer to infer mechanical properties of the soil or rock mass surrounding the borehole such as the indirect tensile strength. There is no mention of a motor controller, only a pump and therefore the pressures must be controlled manually. The logical pressure sources for this testing must be compressed gas, such as nitrogen or oxygen. This device cannot in any fashion be compared with the subject invention which employes the motorized controller that eliminates the need for an operator once the click on the computer screen occurs.

The test procedure is stress-controlled, meaning that the operator applies predetermined pressure levels and observes the resulting deformation (volume change). Stress-controlled testing produces fewer measurement points and less detailed stress-strain information than strain-controlled testing, where small incremental volume changes are imposed and the resulting pressure response is measured. The system relies on an external pressure source, such as compressed gas, which must be regulated manually from the surface. The patent does not describe any motorized actuation. Consequently, the testing process depends on manual pressure regulation and operator control, requiring a highly skilled operator.

Since the device in this patent operates through externally applied pressure rather than internally controlled displacement, it does not provide the same level of precision or automated control that modern strain-controlled pressuremeter systems can achieve.

U.S. Pat. No. 8,776,583 B2 to Marchetti, which is incorporated by reference, describes an in-situ device for soil investigation that cannot be used with the Shaban PMT to provide accurate soil strengths and soil stiffnesses amounts for over a half dozen reasons.

First, the Marchetti's Dilatometer (DMT) controller houses a linear electric motor that injects pressures from compressed gas cylinders into the flat-bladed probe that is pushed into the soil. The volume of compressed gas injected into the DMT probe is not recorded. During PMT testing, the volume of the fluid injected into the PMT probe must be recorded to produce the soils strength-deformation response.

Second, during DMT testing only three pressures were recorded. Therefore, the Marchetti equipment is not compatible with PMT equipment, which requires a minimum of 20 data points during testing.

Third, the flat-bladed DMT probe is about 96 mm (3.78 inches) wide, 15 mm (0.6 inches) thick, and similar in size to a human hand. During testing, this flat blade is threaded to high-strength steel rods and hydraulically pushed to a desired testing depth. During testing pressures are applied to the dilatometer using tubing connected to compressed gas. This process causes the 60 mm (2.36-inch) diameter thin circular metal plate, mounted with screws on one side of the blade, to be expanded 1.1 mm into the soil. The volume of compressed nitrogen used per DMT test is relatively small (estimated at much less than 0.5 cubic centimeters), as it is needed only for filling the pneumatic tube and expanding the membrane 1.1 mm against the soil pressure.

Fourth, if this Marchetti DMT Control Unit is connected to the PMT probes this volume of compressed gas would not be sufficient to even record a single data point.

Fifth, the DMT circular metal plate in Marchetti is not in any fashion a balloon as it cannot hold any water, or similar material within itself as it expands. Therefore, it cannot be used during any PMT testing.

Sixth, only three soil response readings are recorded at the depth of testing in Marchetti during each test, which are limited to an initial pressure before expansion, a maximum pressure once the 1.1 mm expansion is completed, and a third pressure once the membrane is deflated to its original position. These three recorded pressures only provide indirect information about the soil stiffness from DMT testing. These DMT stiffnesses are significantly different than the PMT stiffnesses, being four or five times higher than PMT stiffnesses (e.g., at a single depth DMT stiffnesses may be 8000 psi while PMT stiffnesses may be 1500 psi). Therefore, DMT and PMT stiffnesses are not comparable.

Seventh, the control unit used for the Marchetti DMT testing cannot inject any water or similar fluid into the circular metal plate, since it is expanded with pressures injected through a regulator that is required to be attached to a compressed gas tank.

Eighth, the Marchetti probe does not inflate in a radial direction as required by the subject invention. Marchetti's 60 mm (2.36 inch) diameter plate expands in an arching manner on one side of the blade into the soil during testing.

Nineth, the subject invention PMT probe expands radially in all directions and produces the same radial displacements along its entire length (i.e., which can be analogous to a Ball Park Frank that plumps when you cook it). The subject invention PMT expansion has the same strain long any plane along the length of the probe) which cannot be achieved by the Marchetti DMT testing.

Tenth, Marchetti injects only a small amount of compressed gas (less than 0.5 cubic centimeters) compared to the 150 cubic centimeters injected during PMT testing required by the subject invention.

Finally, the Marchetti's controller cannot perform PMT testing as required by the subject invention. Marchetti only records three pressures during testing, with only one of those three used to determine a DMT stiffness, while the subject invention equipment records at minimum 20 pressures as equal increments of water are injected into the probes.

The ROCTEST TEXAM® PMT by manufactured by Roctest Ltd. in Saint-Lambert, Quebec, Canada, is a preboring PMT (i.e. requires a borehole prior to placement and testing) that provides in-situ stress-strain curves and is well known. However, the ROCTEST TEXAM® requires a hand crank, which must be physically rotated by an operator to be used. It also weighs approximately 70 pounds and requires two people to transport and assemble. This PMT is no better than the PMT used in the Shaban thesis previously described.

Thus, the need exists for solutions to the problems with the prior art.

The subject invention requires a control unit that can be run with the simple push of a button or mouse click, therefore eliminating the need for a highly skilled operator and eliminating any hand crank tool. The subject invention allows a person with a high school education to run tests and produce very high-quality data.

The fully automated controller, in the subject invention, incorporates a motor controller with an encoder that drives the electric motor of the electro-hydraulic linear actuator. The electric motor is mechanically coupled to the hydraulic cylinder through a mounting bracket assembly. The bracket is secured to the electric motor using fasteners and is attached to the cylinder body using a bolt-and-nut connection or equivalent fastening mechanism. This bracket provides structural support and maintains alignment between the motor and the actuator assembly. The output shaft of the electric motor is connected to the actuator shaft of the cylinder through a shaft coupling. The shaft coupling mechanically links the motor shaft to the cylinder drive shaft. The motor controller receives command signals from the data acquisition (DAQ) system and regulates motor operation using pulse-width modulation (PWM) to control actuator speed and displacement. The motor automatically adjusts the torque required to produce precise volumes of water (e.g., approximately 5 $cm^3$) during equal time increments during tests of soils with varying strengths and stiffness. This feature produces the most reliable test data possible from PMT testing.

The subject invention automatically records all the necessary data points throughout the test with precise volumes of water injected over consistent rates, thereby eliminating the problems in Shaban and guaranteeing high-quality results.

SUMMARY OF THE INVENTION

A primary objective of the present invention is to provide devices, apparatus, systems and methods for providing in-situ soil testing with a motorized compact PMT with a balloon probe placed into soil, to automatically produce accurate soil strengths and stiffnesses in a single push-button or mouse click operation by a field technician without requiring operators with a PhD, all within approximately 5 minutes.

A secondary objective of the present invention is to provide devices, apparatus, systems and methods for providing in-situ soil testing with a motorized compact PMT with a balloon probe placed into soil, using a strain-controlled procedure either using continuous injection or with up to about 20 pressure recorded data points as the balloon probe is inflated to approximately 50 percent from an initial borehole wall inflated position to calculate soil strengths and stiffnesses in a single operation.

A third objective of the present invention is to provide devices, apparatus, systems and methods to accurate accurately calculate soil strengths and stiffnesses with a compact motorized PMT which automatically adjusts the torque required to test soils of varying strengths and stiffness, in a single operation within approximately 30 seconds.

A fourth objective of the present invention is to provide a safe, reliable, and fast alternative that produces soil stiffnesses, strengths and deformations, without measuring densities based on radiation recordings.

A fifth objective is to present a relatively light weight (only up to approximately 35 pounds) motorized controller for PMT testing that is operated and produces test results with a one-step push button or mouse click operation.

A sixth objective of the present invention is to provide devices, apparatus, systems and methods for providing in-situ soil testing produces data that can be used for applications other than compaction QC, including designs of various foundations for buildings, evaluations of existing foundations for buildings, and evaluations of existing soil strengths.

A seventh objective of the present invention is to provide devices, apparatus, systems and methods for providing in-situ soil testing produces data, that eliminates any Nuclear Regulatory Commission (NRC) concerns and produces savings for the companies.

A preferred embodiment can include an external computing device, such as a laptop, with APMT© software installed, connected through a communication interface to the controller unit, housing an on/off switch, a power source, an electronic motor. A motor controller with encoder, a relay switch, a data acquisition system, a hydraulic cylinder assembly, a pressure sensor, and an analogue pressure transducer. A ground engaging balloon probe with tubing is connected through a quick connect coupling to the test port on the control unit. A separate quick connect coupling is connected to an external water supply, typically a jug of distilled water, used to saturate the tubing, and cylinder in the control unit prior to testing. A single switch for the controller unit housing causes turns the system on, the external computer software connected to the controller, allows the operator to start a test by clicking on the start button causing the electric motor controller to engage the motor and pump water through the tubing and from the saturated cylinder, to radially inflate the balloon using either equal water volumes in up to approximately 20 increments or continuously injecting water until the balloon is approximately 50% larger than an initial filled position when the inflated balloon is first in contact with walls in the borehole. The APMT© software records, pressure data during each volume increment, and then calculates soil stiffness and soil strength of the soil around the borehole. This pressure and volume data is obtained and evaluated during a single operation that runs within approximately 5 minutes.

The conduit can include tubing. The tubing can include lengths between approximately 30 to approximately 5 feet long.

The electric motor with the built in encoder can include stepper or linear motors.

The system can further include quick connect connections between the variable length conduit and the housing.

The pump can include a cylinder and piston and a data acquisition card.

The system can further include a switch, on the housing, which when activated allows the motor to inject fluid into the probe while soil resistance pressures and balloon volumes are recorded.

The system can include a handheld transport container with a handle, the container having dimensions of approximately 8 inches by approximately 18 inches by approximately 24 inches.

The container can include an overall weight between approximately 25 to approximately 35 pounds.

The system can include at least one USB or similar communication port on the housing for allowing said data to be downloaded from the computer.

The system can include a port on the housing for recharging the battery.

The external fluid supply can include a distilled water supply, typically a jug.

The data can include soil resistance pressures (in Units such as pounds per square inch or kilonewtons per meter squared and balloon volumes (in Units such as cubic inches or cubic centimeters) are recorded.

Another embodiment of the compact portable system for determining soil strengths and stiffnesses and deformations of soil without emitting radiation into surrounding soil, can include a controller unit housing an external computing device, such as a laptop or tablet, with APMT© software installed, connected through a communication interface to the controller unit, housing an on/off switch, a power source, an electronic motor, a motor controller with encoder, a relay switch, a data acquisition system, a hydraulic cylinder assembly, a pressure sensor, and an analogue pressure transducer. A motor, tubing with connectors to an external fluid water supply or jug with pump, and rechargeable battery power supply, a ground engaging probe having an inflatable probe covered in a flexible membrane to be placed into soil, and a conduit attached between the pump in the controller unit and the inflatable membrane, wherein the electric motor pumps fluid through the conduit into the inflatable membrane, which is inflated and deflated from saturated control unit, and sensed data is used to provide soil stiffness, soil strength, and soil deformations of the soil, without emitting any radiation into the soil.

The sensed data can include soil resistance pressures (in Units such as pounds per square inch or kilonewton (kN) per meter squared and balloon volumes (in Units such as cubic inches or cubic centimeters) are recorded.

The inflatable membrane can include a fixed-length radially expanding long cylindrical balloon.

The compact probe and controller can further include a computer to provide the soil stiffness, the soil strength, and the soil deformations of the soil.

Further objects and advantages of this invention will be apparent from the following detailed description of the presently preferred embodiments which are illustrated schematically in the accompanying drawings.

BRIEF DESCRIPTION OF FIGURES

The drawing figures depict one or more implementations in accordance with the present concepts, by way of example only, not by way of limitations. In the figures, like reference numerals refer to the same or similar elements.

FIG. 6A is a side view of a cylindrical support used the supports in FIG. 5.

FIG. 6B is a front view of the cylindrical support of FIG. 6A.

FIG. 7A is a side view of an electrical motor support used in FIG. 5.

FIG. 7B is a front view of the electrical motor support of FIG. 7A.

FIG. 10B shows a schematic hydraulic cylinder, water injector as the piston is in the fully retracted water in position.

FIG. 10C shows a schematic hydraulic cylinder, water injector as the piston is in the partially extended water out position.

FIG. 11A is a top view of the pump/motor and data acquisition equipment mounted to the mounting plate set inside the control unit 1.

FIG. 11B is an isometric view pump/motor and data acquisition equipment mounted to the mounting plate set inside the control unit 1 of FIG. 11A.

FIG. 12 is the motorized APMT© screen showing internal pressure and volume equipment indicators with key motor controlling and testing limit adjustments.

FIG. 13 is the motorized APMT© screen showing pressure, volume, and testing status indicators during tests.

FIG. 14 is a motorized APMT© testing screen with start/stop/test complete buttons, key probe size and location information, raw and or reduced test data using the membrane and volume calibration files given.

FIG. 15 shows a graph of up to approximately 20 data points from the motor operated PMT tests with the invention.

DESCRIPTION OF THE PREFERRED EMBODIMENTS

Figures 1A, 1B:
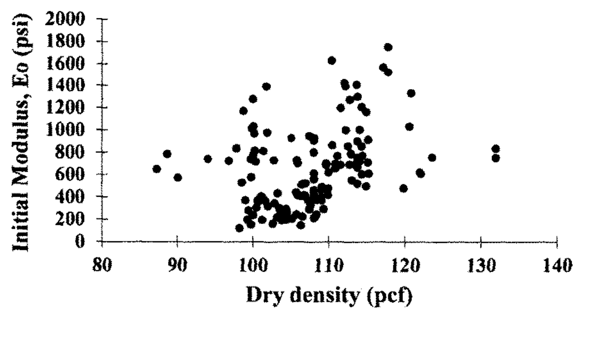
FIG. 1A is a graph of data from the prior art device shown in FIG. 3 with Initial PMT Modulus, $E_0$ (psi) versus Dry density in pounds per cubic foot.
FIG. 1B is a graph of data from the prior art device of FIG. 3, with PMT Limit Pressure pl (psi) versus Dry density in pounds per cubic foot.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein.

Rather, these embodiments are provided so that this disclosure will be thorough and complete, and will convey the scope of the invention to those skilled in the art. Like numbers refer to like elements throughout, and prime notation is used to indicate similar elements in alternative embodiments.

Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise specifically noted, articles depicted in the drawings are not necessarily drawn to scale.

The basis for the PMT theories is the assumption that the PMT probe used in the subject invention causes the soil to expand according to plane strain conditions. Plane strain typically occurs when movements in one direction are significantly longer than the other direction.

The PMT probe part of the subject invention is thus considered to be an infinitely long cylinder, expanding uniformly in the radial direction. This assumption allows the soil moduli to be determined based on linear elastic theory.

The soil limit pressure is determined from the stress versus strain data as the pressure at which the volume of the cavity doubles that the PMT probe is placed.

The data in FIG. 1A and FIG. 1B show that both the modulus (stiffness) and strength (limit pressure) vary significantly at a given density. For example, at a density of 100 pounds per cubic foot (pd), the stiffness varies from below 200 to over 1400 pounds per square inch (psi), while the strength varies from below 10 to nearly 80 psi.

Soil compaction state of practice QC acceptance criteria has remained the same for over 60 years, as field data, reported in terms of moisture and density are checked against standards based on lab tests. Although lab-based soil compaction testing is relatively simple and consistent; no stress-strain, stiffness or ultimate strength data are derived from it.

Under Florida Department of Transportation (FOOT) Contract BDV 28 977-04 and in conjunction with the dissertation of Shaban, small diameter PMT (SDPMT) equipment was developed and tested at four locations on and near the Florida Institute of Technology (Florida Tech) campus along Florida's Space Coast. SDPMT probes 6-, 8-10- and 12-inches in length and ¾-inch in diameter were manufactured. These probes fit in the same hole that is made using the drive pin during NDG testing. During this research, the 6-inch and 12-inch probes were used for testing, enabling both 6- or 12-inch unbound pavement layers to be evaluated.

The invention is a safe, reliable, and fast alternative that produces soil strengths and deformations, instead of densities based on radiation recordings.

A list of the components in the figures will now be described.

Figure 3:
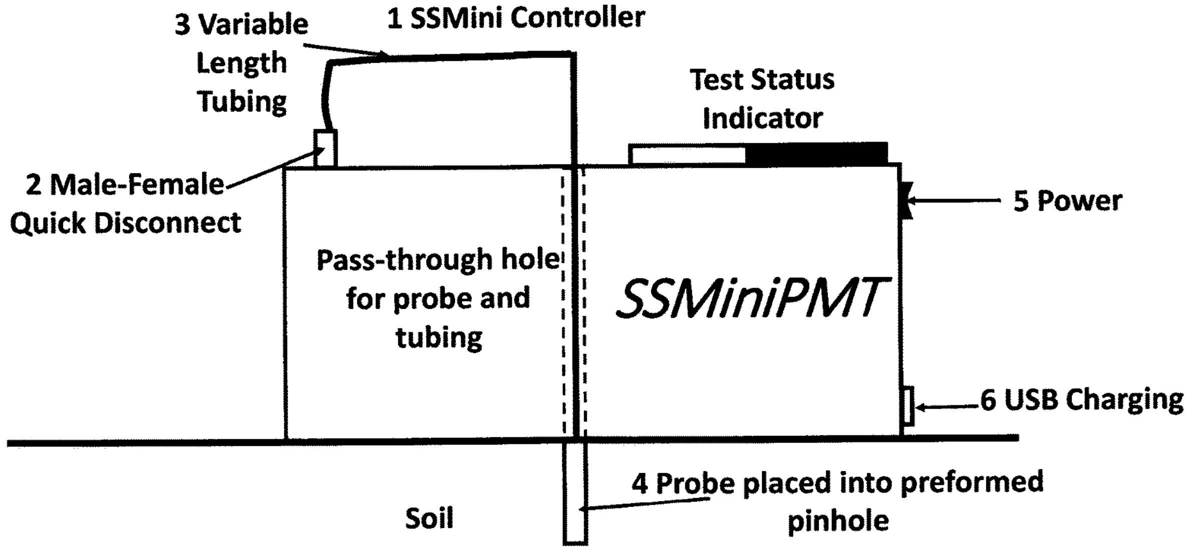
FIG. 3 is a side view of the novel controller unit with a conduit/tubing connector to the ground engaging probe.

PA. prior art 50-pound nuclear density gauge (NDG)
1 Controller unit
2 Quick Connect Coupling for Saturation
3 Quick Connect Coupling for Testing
4 Tubing
5 On/Off Power switch
6 Battery Charging Station
7 Probe
8 Communication Interface, USB ports
10 Electric Motor with Encoder
11 MD (Motor Driver Circuit)
13 Pressure Sensor
14 Analog Pressure Gauge
15 HC Hydraulic Coupling) (right)
16 Relay Switch
17 Valve
18 Water supply (Water Jug)
19 Filters
20 Hydraulic cylinder pump (water injector)
25 Piston
30 Computing Device
35 Data Acquisition Card
40 Power Source
50 Test Status
60 Cylinder Piston Support(s)
70 Electric Motor Support(s)
80 Internal Mounting Plate
82 Motor with Encoder/Hydraulic Water Injector Cylinder Mounting Fasteners
84 DAQ Mounting Fasteners FIG. 3 is a side view of the novel controller unit 1 with conduit/tubing connector 3 to the ground engaging probe 4.

Figure 4:
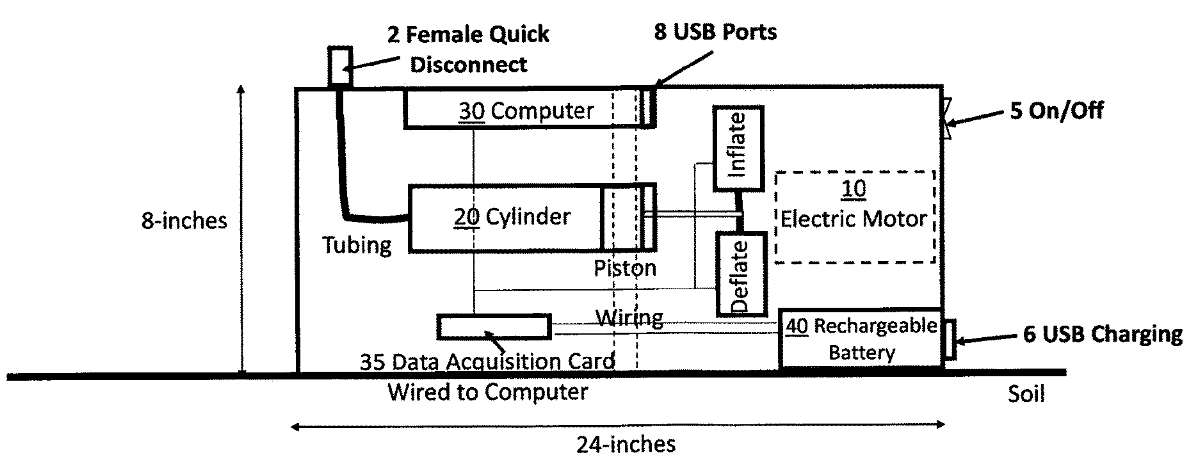
FIG. 4 is a side cross-sectional view of the controller unit of FIG. 3 without component supports.

FIG. 4 is a side cross-sectional view of the controller unit 1 of FIG. 3 without component supports 60, 70.

Figure 5:
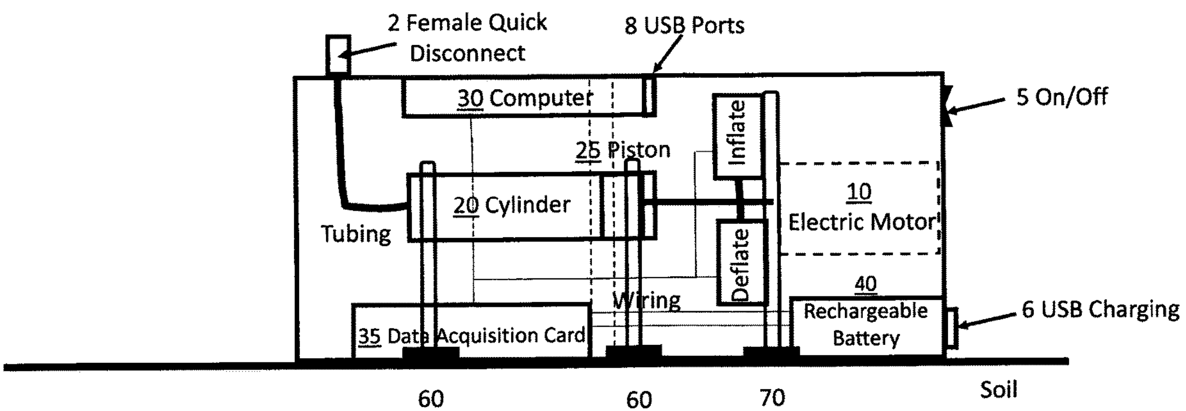
FIG. 5 is another side cross-sectional view of the controller unit of FIG. 3 including supports.
Figure 8:
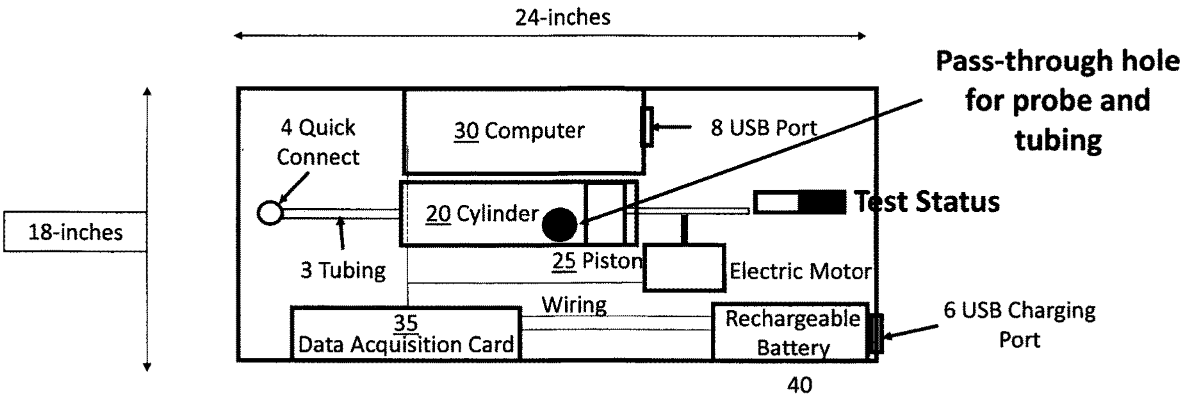
FIG. 8 is a top view of the controller unit of FIG. 3 excluding supports.

FIG. 5 is another side cross-sectional view of the controller unit 1 of FIG. 3 including Cylinder Piston Supports 60 and Electric Motor Support(s) 70

Referring to FIGS. 3-7, the controller unit 1 can include a housing having a height of approximately 8 inches, by approximately 24 inches long by approximately 18 inches wide, and can have an overall weight between approximately 25 lbs. to approximately 35 lbs.

An electric motor 10 such as a stepper or linear motor can operate a pump having a cylinder 20 and piston 25 that pumps a fluid, such as water through a tubing conduit 4 to a ground engaging balloon probe 7, such as but not limited to any current mono-cell PMTs, including the PENCEL and TEXAM probes manufactured by Roctest, Ltd., and the SSMini probes manufactured by Cosentino Engineering Instrumentation Systems, LLC, and are not sold to the public.

A soil balloon test with the controller 1, produces in-place soil strengths and/or stiffnesses/and/or deformations within a properly sized hole in the soil, in which the rubber cylindrical balloon 7 is placed, then inflated and deflated.

The controller unit 1 can be equipped with electric step or linear motors 10, a rechargeable battery 40, valves 17, ¾-in OD tubing 4 such as McMaster Carr Part 51225K42 tubing, a rugged laptop field computer 30 such as a Panasonic Toughbook with software and associated electrical connections and wiring.

Figure 9:
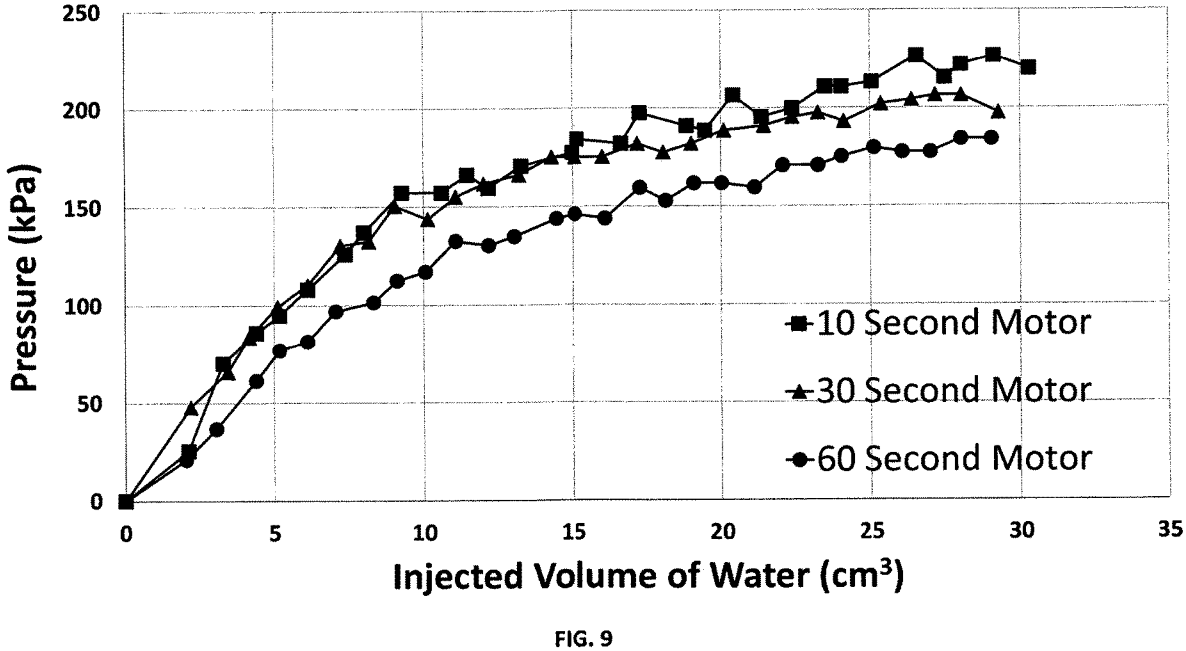
FIG. 9 shows a graph of test data with test durations of 10, 30, and 60 seconds using the novel invention.

FIG. 9 shows test data from test durations of 10, 30, and 60 seconds as the probe is expanded in the air during typical membrane calibrations for volumes of up to 30 $cm^3$. The data in FIG. 9 represent membrane calibration tests with the SSMini 6-inch-long probes conducted using a motor to inflate the probe. Waiting 60-seconds between readings produced the lowest membrane resistance, while waiting 10 and 30 seconds produced similar results with the 30-second data being slightly lower than the 10 second data. Since rubber behaves differently at different loading rates, (i.e., at slower loading rates it moves more between increments than at faster rates) these differences are expected results. They indicate two key findings 1) that motorized testing produces expected pressure versus volume results and 2) it is possible to efficiently program the motor for different testing scenarios and produce accurate results. If these tests were performed using the handle and an operator to turn the handle to inject the water, numerous trials would have been required to produce consistent results.

Figure 10A:
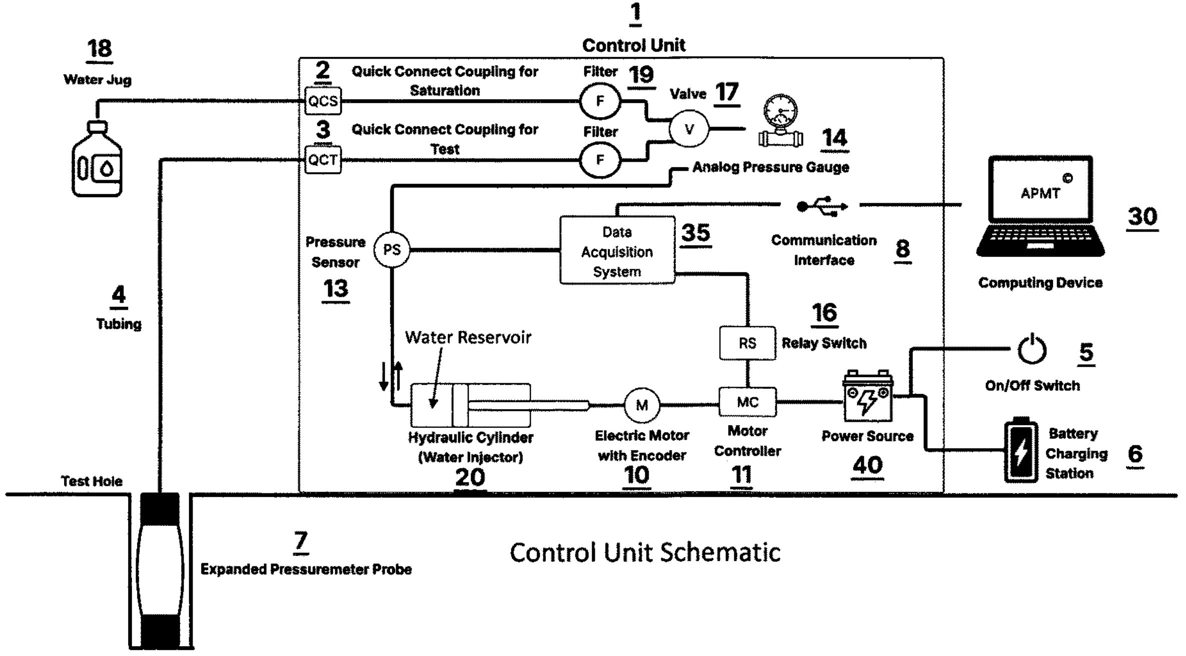
FIG. 10A shows a schematic of the controller with the internal components used to perform PMT tests automatically.

FIG. 10A shows a schematic of the controller 1 used to perform motorized PMT tests. The initial step for using the equipment is to first saturate the hydraulic cylinder 20, tubing 4, and then the tubing and probe using the water jug 18 the quick connect coupling for saturation 2. Arrows within FIG. 10A show the directions of water flow to and from the water reservoir within the hydraulic pump.

FIG. 10B shows the hydraulic cylinder in the hydraulic cylinder pump (water injector) 20 in the fully retracted position which enables water to completely fill the cylinder volume, while FIG. 10C shows the hydraulic cylinder in the hydraulic cylinder pump (water injector) 20 in the partially extended position, which when fully extended enables water to be completely evacuated from the cylinder. This fully extended position is used at the start of the control unit saturation process. The tubing 4 connected to the open end of the quick connector used for saturation 2 is placed in the water jug, then the cylinder is extended fully, forcing all water from the cylinder. This process is then reversed enabling water to be drawn into the cylinder as it is retracted fully as shown in FIG. 10B. When the piston is fully retracted (FIG. 10B), the cylinder, plus the internal tubing is saturated allowing testing to commence.

The motor with encoder 10 is programmed through the DAQ system 35 to perform the saturation by first pushing all water out of the system (FIG. 10 C) then slowly pulling water through the quick connect tubing 2, into the hydraulic cylinder 20 (FIG. 10 B). Once the water is pushed out and pulled back into the equipment, a saturation check is performed using the motorized with encoder 10. The controller 1 has an on/off switch 5, which when activated allows the fully saturated motorized device electric step or linear motor 10 to inject water into the probe 7 while soil resistance pressures (in Units such as pounds per square inch or kN per meter squared and balloon volumes (in Units such as cubic inches or cubic centimeters) are recorded.

Referring to FIG. 10A, a rugged laptop field computer 30, such as but not limited to a Panasonic Toughbook or Dell Latitude 5430 will be used in conjunction with a DAQ 35 such as the National Instruments 6000 series USB Multifunction Data Acquisition Device to record all pressures and volumes necessary to properly conduct equipment saturations, calibrations, and testing.

Stainless steel or equivalent ¾-inch diameter quick-connects 2, 3 such as those available from but not limited to HD Supply or Swagelok can be used to connect and disconnect the tubing from the pump for testing and saturation.

A USB rechargeable battery 40 with an indicator light showing when fully charged, can be used such as but not limited to lithium batteries available from Dewalt, Black and Decker, and others can be used to supply power to the electric motor 10 and computer 30. The battery 40 can be such as but not limited to a 24-volt battery configured to power the motor controller and electric motor. However, other power sources, voltage levels, and power configurations may be used without limitation. Extra ports, such as a side USB port 8 can be used to recharge the battery 40. USB ports 8 are used for data transfer during testing, while USB charging 6 is used to recharge the internal rechargeable batteries 40.

FIG. 5A is a side view of the approximately 4-inch-tall cylinder-piston injection system supports 60 used as the supports 60 in FIG. 4. FIG. 5B is a front view of the approximately 4-inch-tall cylinder support of FIG. 5A. These metallic or plastic components will be attached to the base of the box containing the equipment and secure the cylinder-piston assembly 20,25, enabling both proper transport and testing.

FIG. 6A is a side view of an electric linear or step motor with encoder system used to move the piston 25 within the cylinder 20 during probe inflation and deflation motor support 70 used in FIG. 4.

The data acquisition hardware 35 has been programmed to produce these movements at the specified rate allowing tests to be completed within minutes after probe insertion. FIG. 6B is a front view of the electrical motor support 70 of FIG. 6A, it has a group of small openings for bolt attachments 84 to the motor(s) 10.

Figure 2:
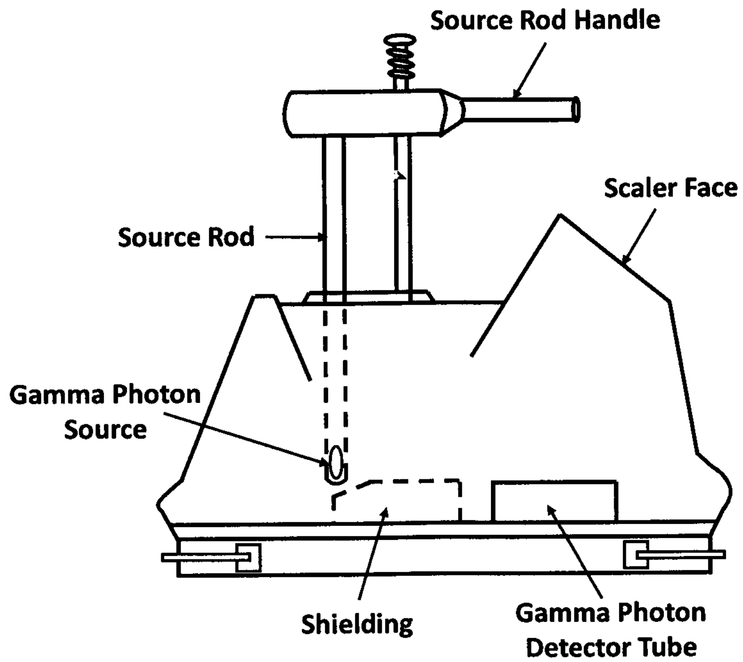
FIG. 2 shows a view of a prior art 50-pound nuclear density gauge; (NDG) portable unit.

FIG. 7 is a top view of the controller unit 1 of FIG. 2 excluding supports 60, 70. It details the USB port 6 that is available for instant download of the test data, the test status lights and the relative locations of the internal equipment, i.e., computer 30, cylinder-piston assembly 20, 25, data acquisition hardware card 35 and rechargeable battery 40.

Referring to FIGS. 3-8, a soil balloon test with the controller 1, can produce in place soil strengths and/or stiffnesses/and/or deformations within a properly sized hole in the soil, in which the rubber cylindrical balloon is placed, then inflated and deflated.

Soil strength in soils varies based on the soil composition. Clays are typically the weakest soils and consequently cause the more engineering problems when building on, in or with them. Civil engineers build most structures to resist a maximum settlement of about 1-inch; therefore, the soil stiffness, which relates settlement to the loads applied by the structure, is critical.

The entire controller 1 can be waterproof sealed from the environment, and it can operate in extreme heat up to approximately 110 degrees F. and cold conditions down to approximately 20 degrees F., throughout the workday.

Water, or a similar fluid can be injected into the probe 7 until it reaches the prescribed volume, from the saturated Bansbach Easylift PD419264-KU-D-001 hydraulic cylinder 20. Once that volume is achieved, the Nidec DCK31 series; 405 006 electric motor with encoder 10 are controlled with the Bansbach ELL-S1 motor controller 11 to deflate the balloon 7, and the test data is converted to soil stiffness and strength.

Once the control unit 1, Bansbach hydraulic cylinder 20, tubing 4 and probe 7 are saturated, with the water jug 18, with an approximately ¾-inch diameter tubing 4 connected to the control unit 1, the hydraulic cylinder and pump 20, can be controlled, via the programmed DAQ 35, using the motor with encoder 10 to either push (inflate) or pull (deflate) water into the probe 4.

Software can be used to first control the electronic motor 10, then record the soil pressures on the cylindrical balloon 7 at the injected volumes as the probes are placed in the properly sized test hole. This same software will produce the soil's resistance pressures as the probe volume is increased and decreased, plus at a minimum elastic moduli and limit pressures.

Because the device is connected to a computer 30, the entire set of data can be stored on the computer 30 and further downloaded through USB or similar communication devices 8 for cloud-based storage devices for immediate use by project managers.

Unlike density and moisture, this set of soil response data can easily be used to map the variations in soil strength and stiffness along the site. Achieving the desired strength ensures that the soil will not fail under the applied loads while the desired stiffness can be used directly to evaluate possible movements of various structures, such as shallow concrete footings, buried drainage or other utility pipes etc.

FIG. 12 is the motorized APMT© screen showing internal pressure and volume equipment indicators with key motor controlling and testing limit adjustments. It provides the operator with key information throughout testing, such as probe is inflating, or deflating.

As shown in FIG. 12, the software can have subroutines that allow a) screens for the operator with indicators that the equipment is functioning as both the analogue and digital pressure and volume information is shown, b) indicators such as the increase inflate and decrease and deflate buttons that allow precise motor control during testing and calibration, c) indicators for the maximum pressure for the internal equipment (i.e., shown as 3000 kPa or in Imperial units that would be 450 psi) d) to set the volume increment for the motor to inject throughout testing e) gauges for returning the volume to zero and to stop the test and to ensure that the calibration is valid.

FIG. 13 is the motorized APMT© screen showing pressure, volume, and testing status indicators during tests.

As shown in FIG. 13 during motorized testing the software can have subroutines that show; a) the pressures and volumes during testing, b) color coded indicators that show the operator what portion of the test is occurring c) indicators to start the test, abort the test, save the test data and exit the subroutine and return to the main software menu. indicators/screens showing storage of the tubing and membrane calibrations, c) storage of the in-situ test data, and d) control of the motor and cylinder-piston assembly used to inflate and deflate the sealed rubber-encased metal probe.

FIG. 14 is a motorized APMT© testing screen with start/stop/test complete buttons, key probe size and location information, raw and or reduced test data using the membrane and volume calibration files given.

As shown in FIG. 14 during motorized testing the software can have subroutines that show; a) completed test data in terms of both the raw uncorrected data and the reduced or corrected data, b) basic probe size information such as length (shown as 150 mm) and key testing information such as depth of test and the control unit height off the ground, plus the distance from the tip of the probe to its center, and c) file paths where the membrane and volume calibration data is stored so that they are correctly applied to the raw data to produce the corrected data.

The all-in-one unit can work with a variety of probes and will deliver accurate stress-strain test results in minutes for any soil tested. The probes are simply inserted into the same NDG drive-pin hole, the start button is pushed, and the probes are gently inflated and deflated using water to produce stiffness and strength data that is simplified for the field technician into acceptable or unacceptable strengths. This data is also available to the engineers allowing a more detailed analysis.

The controller unit 1 quickly and efficiently produces the in-situ stress-strain curve. The resulting data helps engineers develop a picture of the materials strength-deformation properties across the site. It can be used during classical geotechnical compaction and in the unbound pavement layers of roadways. The ¾-inch diameter SSMini PMT probe also allows engineers to evaluate existing pavements by first coring an approximately 1-inch hole then driving the approximately ¾-inch pin into the underlying soils. The various probe lengths allow various layer thicknesses to be evaluated.

Stress-strain curves from the controller unit 1 can be tailored to specific engineering needs and may include unloading and reloading loops. Their data can be used to predict elastic moduli at small strains, which can then be compared to either the design resilient moduli or back-calculated resilient moduli.

Because the controller unit 1 testing has the potential to significantly change current practice, the Florida Department of Transportation and several geotechnical consulting companies are assisting with this research.

FIG. 10A shows a schematic of the controller used to perform motorized PMT tests automatically.

The electric motor 10 can be but is not limited to an off-the-shelf Bansbach EasyMotion Pump/Motor Assembly, such as the 2.95 ft-lbs (4 Nm) Torque, 24 volt model PD419264-KU-D-001. From Bansbach of North America, Melbourne, Florida, United States of America. The electric motor 10 and hydraulic cylinder 20 is shown and described in reference to FIGS. 11A-11B.

Motor Circuit 11 is shown and described in reference to FIG. 11

Pressure sensor 13 can include but is not limited to a Setra 500 psi to 1000 psi gauge pressure transducer with equipped with ¼-inch NPT for connection to the tubing from Boxborough Massachusetts, USA.

Analog Pressure Gauge 14 can include but is not limited to an Ashcroft 600 psi analogue pressure transducer product number PN: 631008S02CXFF600 #/KP Stratford, CT 06614-5145, U.S.A.

The purposes of the analog pressure gauge 14 is to allow an operator to ensure that pressure data is shown. This gauge serves as a backup or quality control check to ensure there is pressure in the tubing during use.

The quick connect hydraulic coupler used for equipment saturation before testing (Hydraulic Coupler) 2 15 can include but is not limited to a Swagelok Instrumentation Quick Connect Body, ¼ in. Swagelok Bulkhead Tube Fitting and an Instrumentation Quick Connect Stem without Valve, ¼ in. Swagelok Tube Fitting.

A quick connect hydraulic coupler is used for testing Left HC (Hydraulic Coupler) 3 16 can include but is not limited to a Swagelok Brass Instrumentation Quick Connect Body, ¼ in. Swagelok Bulkhead Tube Fitting and a Brass Instrumentation Quick Connect Stem without Valve, ¼ in. Swagelok Tube Fitting.

The external Water Jug 18 can include distilled water and include approximately ¼, ½, 1-, or 2-gallon jug, preferrable 1 gallon available from any supermarket. The tubing 4 is secured into the top of the water jug 18 and placed in the water to perform the saturation process. The water jug can have an upper opening and can have a flat bottom that allows the jug to stay upright when rested on the ground. The jug can have a handle for being easily transported.

FIG. 10. depicts the off-the-shelf components mounted inside the controller unit 1 as a pressuremeter probe 7 that is connected to the quick connect hydraulic coupling 3 for testing is expanded into the test hole. It includes Swagelok connectors, ¼-inch high pressure tubing 4, Bansbach motor 10, controller 11 and cylinders 20, a Setra pressure transducer 13 and a National Instruments Data Acquisition Card 35. Swagelok, or equivalent hydraulic connectors are used with ¼-inch high pressure tubing to connect all components in the controller and to the probe.

Swagelok or equivalent quick connect stems 2, 3 are mounted to the control unit face, for connection to the corresponding quick connect body 2, 3 and external tubing 4. Two in-line Swagelok filters (90 and 140 microns) 19 are plumbed into the system to prevent contaminants (soil) from traveling into the hydraulic cylinder 20. The quick connect hydraulic couplings 2, 3 are used to connect the tubing to system saturation equipment and associated pressuremeter probe 7 to the controller 1. One quick connect 3 is used for conducting pressuremeter tests, including calibrations, the second quick connect 2 is used to perform control unit and tubing/probe saturations. A valve 17 is used to switch between the two quick connectors 2, and 3 to either saturate the equipment (all tubing and hydraulic cylinder 20 or conduct tests. The tubing 4 from this second connection 2, would be placed into a portable water supply consisting of distilled water jug 18, with anti-freeze fluid added if needed. Anti-freeze would be needed in climates, such as winter climates where the novel pressuremeter is being used when temperatures go below freezing (below 32F).

The external computing device with the required APMT© software installed 30 controls the desired testing sequence for pressuremeter testing. It is connected via USB or equivalent type communication connectors 8 to the National Instruments (NI) USB NI-DAQmx or equivalent data acquisition (DAQ) card 35 mounted to the internal mounting plate 80 in the control unit (FIG. 11A and FIG. 11B). Once powered on, the power source 40, which is wired to the DAQ card 35, when activated from the software, engages the Bansbach Easymotion electric motor 10, through the Bansbach ELL-S1 motor controller 11, which is wired to the DAQ card 35, to allow it to move the Bansbach Easymotion piston in the cylinder 20 to inject the fluid from the saturated control unit 1 through the tubing 4 and into the pressuremeter probe 7.

The Bansbach electric motor with the built-in encoder 10 (FIG. 11A and FIG. 11B) is mechanically coupled to the hydraulic cylinder water injector 20 through a mounting bracket assembly. The bracket is secured to the electric motor using fasteners and is attached to the cylinder body using a bolt-and-nut connection or equivalent fastening mechanism placed on an internal mounting plate. This bracket provides structural support and maintains alignment between the motor and the actuator assembly. This entire pump motor assembly is then secured to an internal mounting bracket 80 with fasteners 82 as shown in FIG. 11A and FIG. 11B.

The output shaft of the electric motor 10 is connected to the actuator shaft of the cylinder 20 through a shaft coupling as shown in FIG. 11A and FIG. 11B. The shaft coupling mechanically links the motor shaft to the cylinder drive shaft. The rate that the cylinder advances is controlled by the motor encoder 10 and monitored to determine the volume of water and the pressure transducer 13 is plumbed into the tubing on the outflow side of the cylinder. The Setra or equivalent pressure transducer 13 is equipped with voltage input and output connections. Volumes for probes 7 with up to approximately 150 $cm^3$ (9.15 $in^3$) required during testing, are recorded based on the revolutions of the electric motor with encoder 10 and calibrated to the fixed zero location of the piston with an empty hydraulic water injecting cylinder 20. Pressures are recorded at the desired water volume injection intervals up to the limit of the pressure transducers or approximately 7000 kPa or 1000 psi. The 600 psi (4000 kPa) Ashcroft PN: 631008S02CXFF600 #/KP or equivalent analogue pressure gauge 14 is used to constantly check or ensure that the equipment is working and can be used to record pressure data manually if necessary.

FIG. 11A is a top view of a motor pump assembly 20 plus data acquisition system 35 in FIG. 10A. The motor and encoder 10 can be a Bansbach's PD419264-KU-D-001 motor with the pump motor bracket. The 2.95 ft-lbs (4 N·m) torque, 24 volt, Bansbach PD419264-KU-D-001 electric motor 10 can be mechanically coupled to the 150 $cm^3$ Bansbach hydraulic cylinder 20 through a mounting bracket assembly. The bracket is secured to the electric motor using fasteners and is attached to the cylinder body using a bolt-and-nut connection or equivalent fastening mechanism. This bracket provides structural support and maintains alignment between the motor and the actuator assembly. This entire pump motor assembly is then secured to the internal mounting bracket 80 with fasteners 82 as shown in FIG. 11B. The data acquisition system 35 can be an NI DAQ such as the National Instruments 6000 series USB Multifunction Data Acquisition Device is mounted to the internal mounting plate 80 with DAQ mounting fasteners 84 and subsequently secured inside the control unit 1 using the internal mounting plate 80 as depicted in FIG. 11A and FIG. 11B.

As the electric motor with encoder 10 shaft rotates, it moves the piston inside the hydraulic cylinder 20 to allow either probe 7 inflation or deflation. The output shaft of the electric motor encoder 10 is connected to the actuator shaft of the hydraulic cylinder 20 through a shaft coupling. As the electric motor with encoder 10 rotates the actuator shaft within the hydraulic cylinder 20 in either the positive or negative direction, the piston moves in and out thereby moving water in and out of the hydraulic cylinder 20. The volume of water moved per shaft coupling rotation is measured and related to the voltage and set as a calibration constant in the DAQ software 35. The shaft coupling mechanically links the electric motor with encoder 10 shaft to the hydraulic water injecting cylinder 20 drive shaft. It can be connected to the preprogrammed data acquisition system 35 so that it supplies the required torque, and shaft rotation rates to control the injection of fluid as the piston advances through the attached Bansbach Cylinder Piston/Motor with encoder 10 and controller unit into the accompanying pressuremeter probe 7.

The motor driver power source, can also be supplied by Bansbach, produces the required voltage through programming of the data acquisition equipment to control the motor based on the percent of full-scale of the internal cylinder movement. The internal circuitry of the assembly would control the input voltages based on the data acquisition software programming to start and stop the motor at the desired torques, shaft rotations, and associated volumes of fluid to perform the required pressuremeter test.

As discussed, the pump/motor assembly 20 in FIG. 10A can be a Bansbach PD419264-KU-D-001, 2.95 ft-lbs (4 Nm) Torque, 24-volt motor with the pump motor bracket, Bansbach of North America Melbourne Florida U.S.A.

FIG. 11A is a side cross-sectional view of the pump/motor assembly.

FIG. 11B is an isometric view of the pump/motor assembly of FIG. 11A.

FIG. 12 is the motorized APMT© internal sensor equipment indicator checks with key analogue plus digital pressure and volume information. It will be used by operators to ensure that the digital sensors are providing pressures and volumes during testing. It also shows the following test status information: probe is inflating, data is being recorded, probe is deflating, if the test is aborted or if the test is complete. It has test start and test abort buttons, plus a button to save the test data and to return to the main APMT© menu.

FIG. 13 shows an APMT© screen showing pressure, volume and testing indicators during motorized tests. It allows the operator to view the pressures and volumes throughout the test. It includes test start and test abort buttons, plus a button to save the test data and to return to the main APMT© menu. It also shows the following test status boxes which are highlighted according to the testing sequence occurring: ready (for testing), inflating probe, recording data, deflating probe, test aborted, test complete.

FIG. 14 shows a third APMT© screen showing the raw data and corrected or reduced data at the completion of a PMT test. It also basic probe and testing information displayed, plus the storage path locations for the calibration and test files. The raw data corrections, which are subtracted from the raw data to produce the reduced data. They include one correction for the inherent balloon or membrane resistance and the second volume correction for the expansion of the tubing and thinning of the rubber during testing. There is also a third correction for the pressures difference between the control unit and the center of the rubber measuring probe, which is added to the pressure read at the control unit height. Analysis of the reduced data produces a PMT modulus of 73400 kPa or 10, 485 psi and a limit pressure of 3700 kPa or 530 psi, which is displayed for the operator at the conclusion of the test.

FIG. 15 shows a graph of up to approximately 20 data points from the automated motor operated PMT tests with the invention. During this testing, the operator simply clicks the start button on the software and waits until test completion. At the completion of the test the PMT modulus of 6,790 kPa or 970 psi would be determined using the data in the dashed ellipse shown, as the pressure on the borehole wall versus motor injected water volume increase linearly from about 9 $cm^3$ to about 11 $cm^3$. The software will also display a limit pressure as shown in the dashed ellipse around the last few data points as 295 kPa or 43 psi. This data shows the numerous advantages of the motorized system. It can save significant time and be used for a wide variety of complex design and evaluation scenarios.

Any fully automated motorized test data is more precise as it enables the precise water volumes to be injected producing the evenly spaced data along the x-axis or volume of water injected into the probe. This is one of many significant advantages of the fully automated equipment. Other significant advantages include producing highly specialized pressuremeter testing such as that shown in FIG. 15, which could be programmed and motorized to enable evaluations of complex geotechnical engineering concerns such as cyclic loads from vehicles on the roads, waves crashing into the retaining walls along the coastlines, heavy stationary loads from construction equipment like cranes, or extremely critical soil behaviors associated with construction at nuclear power plants.

Other significant advantages include producing highly specialized PMT tests that enable evaluations of complex geotechnical engineering concerns including cyclic loads from vehicles on the roads, waves crashing into the retaining walls along the coastlines, heavy stationary loads from construction equipment like cranes, or extremely critical soil behaviors associated with construction at nuclear power plants. The second major breakthrough from the fully automated PMT controller is that a technician with a high school level education could conduct these if the motorized equipment was preprogrammed to do so. Note, that other highly complex testing processes are also able to be programmed and run with the fully automated controller. This significant advancement in PMT testing will vastly improve its use.

While the embodiment references a portable computer 30, the data can be analyzed by a tablet or smart phone, and/or by hand to calculate and determine soil stiffness, soil strength, and soil deformations of the soil.

This device can be adapted to test any soil at any location since the tubing 4 connected to the controller 1 can be any length. Tubing could easily be approximately 30 to approximately 50 feet from the unit allowing evaluations in small, hard-to-access locations, such as under buildings, near sinkholes, in caves, and other locations.

The term "tubing" can include to flexible tubing, such as but not limited to plastic tubing, rubber tubing, and the like, and can include diameters of up to approximately 1 inch, and preferably approximately ¾ of an inch.

The term "approximately" is similar to the term "about" and can be +/−15% of the amount referenced. Additionally, preferred amounts and ranges can include the amounts and ranges referenced without the prefix of being approximately.

Although specific advantages have been enumerated above, various embodiments may include some, none, or all of the enumerated advantages.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The term "approximately" is similar to the term "about" and can be +/−10% of the amount referenced. Additionally, preferred amounts and ranges can include the amounts and ranges referenced without the prefix of being approximately.

While the invention has been described, disclosed, illustrated, and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A portable motorized pressuremeter for calculating in situ soil properties, comprising;

a controller unit housing connected to a computing device, the controller unit housing an electric motor with encoder, for running a hydraulic piston pump, a pressure transducer, a data acquisition card, a rechargeable battery power supply for providing power to the electric motor and an exterior water supply;

a ground engaging balloon probe connected via tubing to the exterior water supply, the probe to be placed into a borehole in soil with tubing connected to the pressure transducer; and a single switch for the controller unit housing, wherein activating the single switch causes the electric motor to pump water by the hydraulic piston pump from the water supply into the fully saturated hydraulic piston pump to radially inflate the long cylindrical balloon using up to approximately 20 volume increments until the balloon is approximately 50% larger than an initial filled position when the inflated balloon is first in contact with walls in the borehole, and pressure data is recorded at each volume increment, and the computer software accurately calculates soil stiffness and soil strength, from each of the increments in a single operation that runs within approximately ten minutes.

2. The portable motorized pressuremeter of claim 1, wherein the water supply includes:

distilled water supply.

3. The portable motorized pressuremeter of claim 1, wherein the single operation to determine soil strength and stiffness runs within approximately five minutes.

4. The portable motorized pressuremeter of claim 1, wherein the single operation to determine soil engineering properties runs within approximately three minutes.

5. The portable motorized pressuremeter of claim 1, wherein each increment between recordings is between approximately 15 to approximately 30 seconds.

6. The portable motorized pressuremeter of claim 1, wherein the water supply for the control unit is a portable plastic container jug selected from the group consisting of a ¼ gallon ½ gallon, 1 gallon, and 2 gallons, the plastic jug includes a flat bottom portion for allowing the jug to remain upright when resting on a generally level surface.

7. The portable motorized pressuremeter of claim 6, wherein, the water supply is one gallon of water.

8. The portable motorized pressuremeter of claim 7, further comprising:

anti-freeze in the water supply for allowing operation of the pressure meter below freezing conditions.

9. The portable motorized pressuremeter of claim 6, further comprising:

a water supply tubing having one end placed into an upper opening of the jug to below water level in the jug, and a second end attached to a water supply quick connect coupling on the controller unit housing.

10. The portable motorized pressuremeter of claim 9, further comprising:

a probe connection tubing having one end attached to the balloon probe, and a second end attached to another quick connect coupling on the controller unit housing; and a valve inside the controller unit housing to switch between the water supply quick connect coupling and the another quick connect coupling in order to saturate all tubing and the hydraulic pump, or conduct tests for recording volume data and pressure data at each volume increment.

11. The portable motorized pressuremeter of claim 10, wherein the water supply quick connect coupling and the another quick connect coupling are formed from stainless steel.

12. The portable motorized pressuremeter of claim 1, wherein the hydraulic piston pump has a piston head that moves between a retracted position, and an extended position.

13. The portable motorized pressuremeter of claim 1, wherein the probe includes an approximately ¾ diameter.

14. The portable motorized pressuremeter of claim 1, wherein the control unit housing includes dimensions of up to approximately 8 inches by up to approximately 18 inches by up to approximately 24 inches, and includes an overall weight between approximately 25 to approximately 35 pounds.

15. The portable motorized pressuremeter of claim 1, wherein the rechargeable battery is approximately 24 volts.

16. The portable motorized pressuremeter of claim 1, wherein the hydraulic pump has a piston head that moves between a retracted position and an extended position to allow for a saturation process of components in the controller unit housing and to allow for recording volume and pressure data for calculating in situ soil properties.

17. A method for calculating in-situ soil properties with a portable pressure meter onsite, comprising the steps of:

coring an approximately 1-inch hole into a soil surface to form a borehole;

providing a portable ground engaging balloon probe having a diameter of approximately ¾ if an inch, to be inserted into the borehole;

providing a portable controller unit housing an electric motor with encoder, for running a hydraulic piston pump, a pressure transducer, a data acquisition card, a rechargeable battery power supply for providing power to the electric motor and an exterior water supply attaching a controller unit housing connected to a computing device, the controller unit housing an electric motor with encoder, for running a hydraulic piston pump, a pressure transducer, a data acquisition card, a rechargeable battery power supply for providing power to the electric motor;

providing a portable water supply of up to approximately two gallons;

connecting the ground engaging balloon probe to the exterior water supply, the probe; and activating a switch for the controller unit, to cause the electric motor to pump water by the hydraulic piston pump from the water supply to radially inflate the long cylindrical balloon using up to approximately 20 volume increments until the balloon is approximately 50% larger than an initial filled position when the inflated balloon is first in contact with walls in the borehole, and pressure data is recorded at each volume increment, and the computer software accurately calculates soil stiffness and soil strength, from each of the increments in a single operation that runs within approximately ten minutes.

18. The method of claim 17, wherein the water supply for the control unit is a portable plastic container jug selected from the group consisting of a ¼ gallon ½ gallon, 1 gallon, and 2 gallons, wherein the plastic jug includes a flat bottom portion for allowing the jug to remain upright when resting on a generally level surface.

19. The method of claim 17, further comprising the steps of:

providing a water supply tubing having one end placed into an upper opening of the jug to below water level in the jug, and a second end attached to a water supply quick connect coupling on the controller unit housing;

providing a probe connection tubing having one end attached to the balloon probe, and a second end attached to another quick connect coupling on the controller unit housing; and providing a valve inside the controller unit housing to switch between the water supply quick connect coupling and the another quick connect coupling in order to saturate all tubing and the hydraulic pump, or conduct tests for recording volume data and pressure data at each volume increment.

20. The method of claim 17, further comprising the steps of:

providing the hydraulic pump with a piston head that moves between a retracted position and an extended position to allow for a saturation process of components in the controller unit housing and to allow for recording volume and pressure data for calculating in situ soil properties.

* * * * *